United States Patent [19]

Smirmaul

[11] 4,439,025

[45] Mar. 27, 1984

[54] VARIABLE CIRCULAR DUAL IMAGE CORNEAL RADIUS MEASUREMENT INSTRUMENT

[76] Inventor: Heinz J. Smirmaul, 1307 Brookstone La., Duncanville, Tex. 75137

[21] Appl. No.: 292,513

[22] Filed: Aug. 13, 1981

[51] Int. Cl.³ .............................. A61B 3/10; A61B 3/00
[52] U.S. Cl. ..................................... 351/212; 351/247
[58] Field of Search ............................... 351/212, 247

[56] References Cited

U.S. PATENT DOCUMENTS

| | | | |
|---|---|---|---|
| 4,046,463 | 9/1977 | La Russa et al. | 351/13 |
| 4,157,859 | 6/1979 | Terry | 350/35 |
| 4,165,744 | 8/1979 | Cravy et al. | 128/303.1 |

Primary Examiner—John K. Corbin
Assistant Examiner—Rodney B. Bovernick
Attorney, Agent, or Firm—Richards, Harris & Medlock

[57] ABSTRACT

An instrument (20) for measuring the radius of curvature of a cornea (58) of an eye (60) is provided. The instrument (20) includes structure (90, 98, 180) for projecting a reference image (70) onto the cornea (58). The reference image (70) comprises substantially a circle of discontinuous dots (82). A rod (80) of refractile transparent material is provided for optically forming two images (70a, 70b) substantially identical to the reference image (70). Structure (90, 98) is further provided for varying the diameter of the reference image (70) and the two images (70a, 70b) substantially identical to the reference image (70), such that the images form a predetermined image pattern. Structure (36, 38) is provided for measuring the diameter of the reference image (70) when the predetermined image pattern is formed to provide an indication of the radius of curvature of the cornea (58).

20 Claims, 15 Drawing Figures

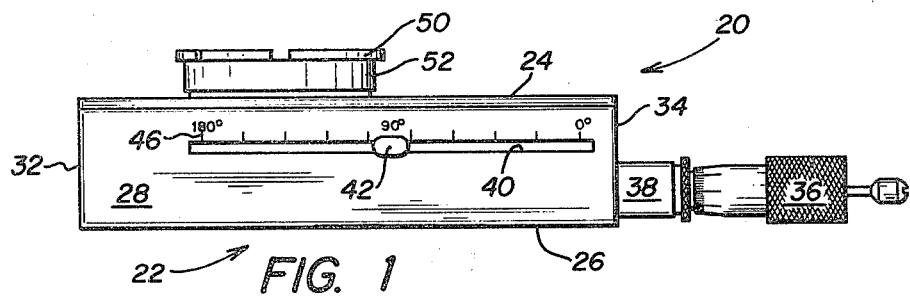
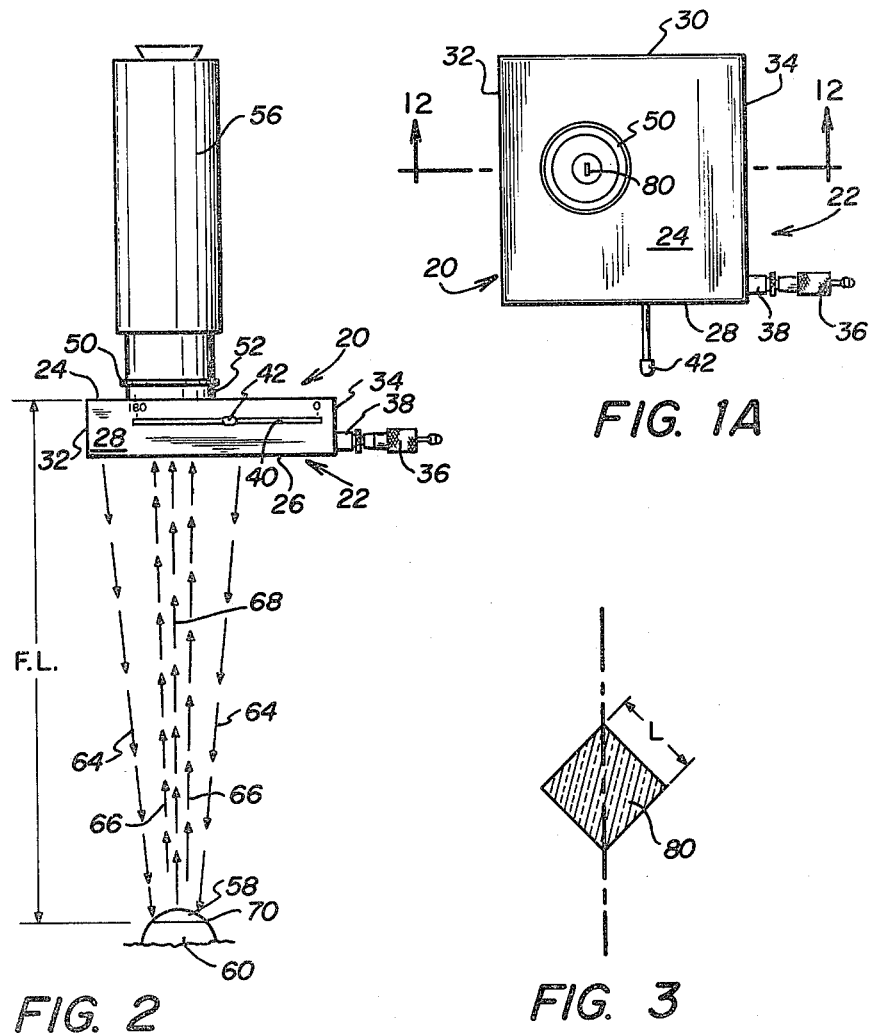
FIG. 1
FIG. 1A
FIG. 2
FIG. 3

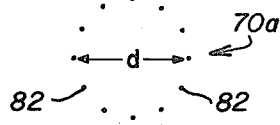
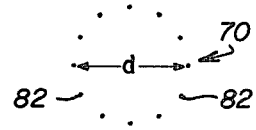
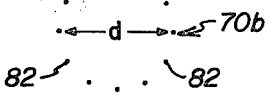
FIG. 4
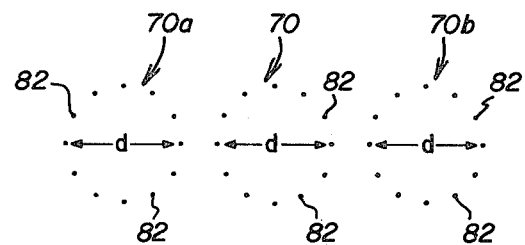
FIG. 5
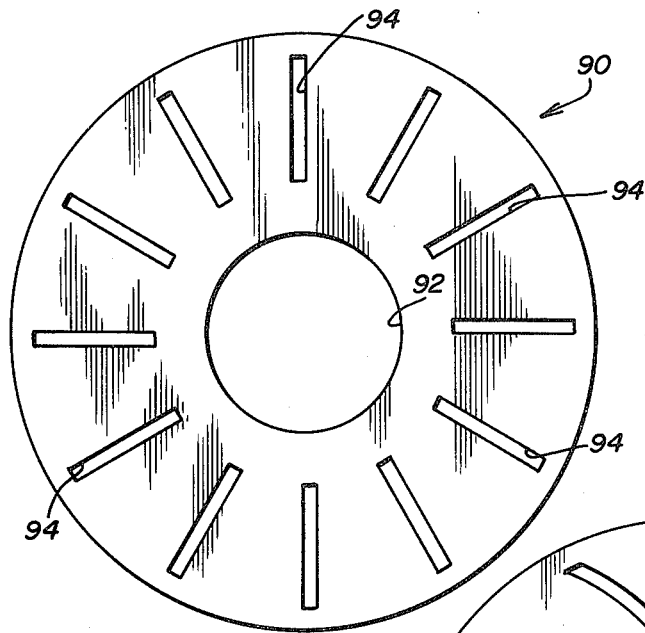
FIG. 6
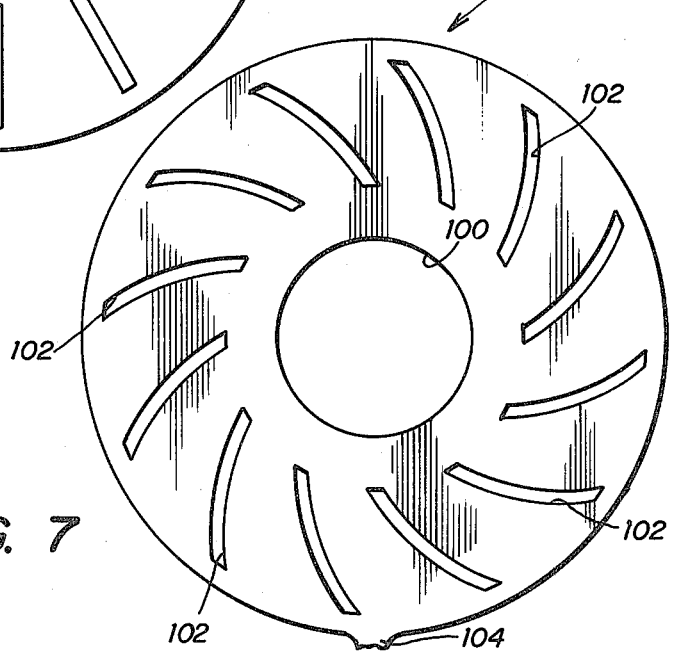
FIG. 7

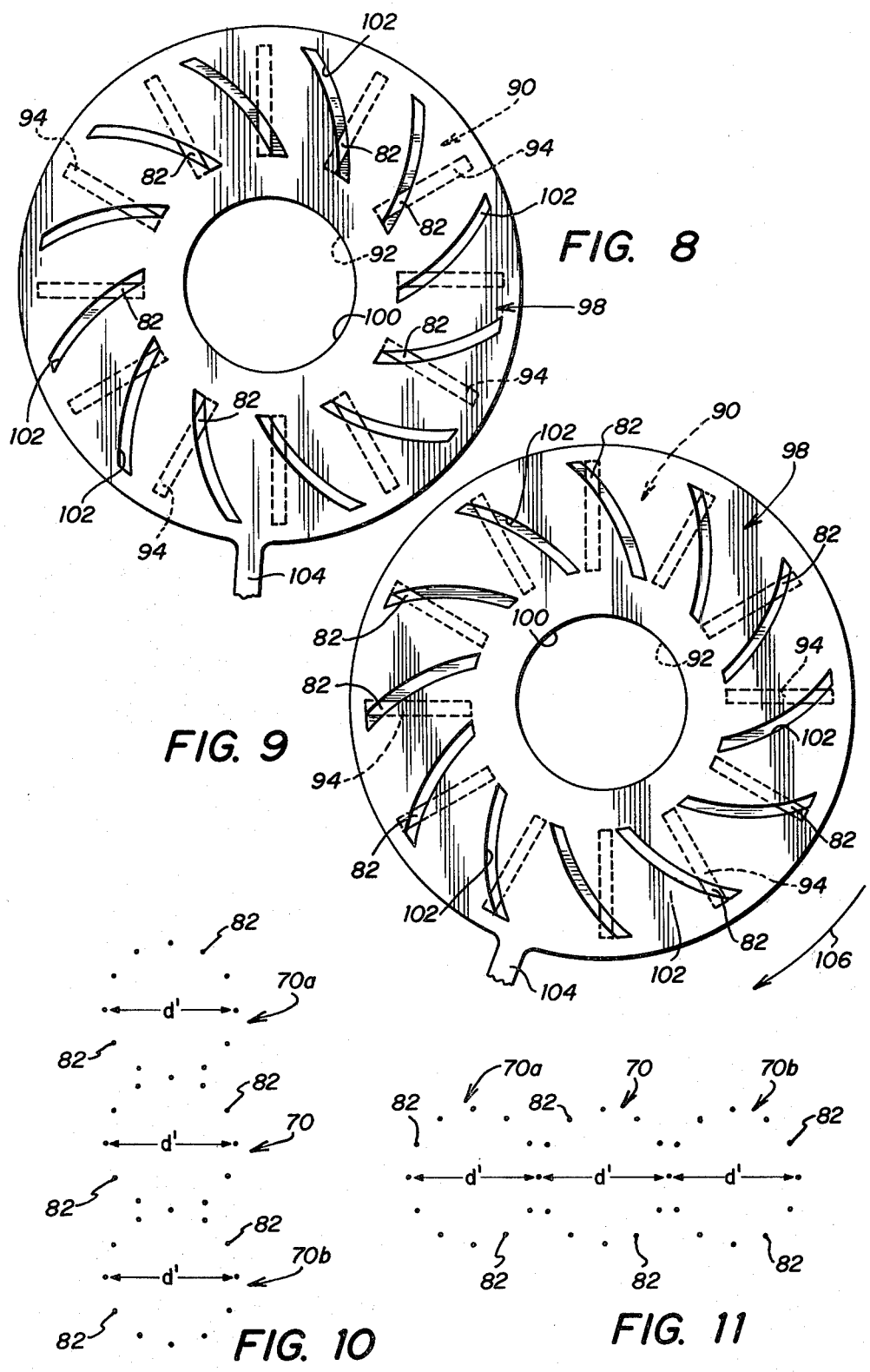

VARIABLE CIRCULAR DUAL IMAGE CORNEAL RADIUS MEASUREMENT INSTRUMENT

TECHNICAL FIELD

This invention relates to surgical instruments for the measurement of the radius of curvature of a cornea of an eye, and more particularly to the use of a variable circular dual image pattern in measurement of the parameters related to the radius of curvature of the cornea.

BACKGROUND ART

The portion of the eye which forms the exterior surface thereof is known as the cornea. For the eye to provide normal vision, the cornea has a spherical shape, an aspherical shape being the cause of a visual defect which is known as astigmatism. Accordingly, providing an indication of the asphericity of the cornea corresponds to providing an indication of the extent of the astigmatism of the eye.

With ophthalmic surgery, for example, surgery involving cataracts and the implantation of intraocular lenses, ideally it is desirable to reconfigure the cornea after the operation to the same radius of curvature existing prior to the operation to thereby prevent or minimize astigmatism. Some operations require astigmatism to be induced at the end of surgery to allow for movement of the cornea during wound healing. In the human eye, the radius of curvature varies from individual to individual with a normal range between 40 and 50 diopters which corresponds to radii of curvature of approximately 8.44 millimeters to 6.75 millimeters, respectfully. In order to ascertain the radius of curvature of the cornea, measurements are taken along certain angles or meridians.

The measurement of the radius of curvature of a cornea may generally be utilized by an ophthalmologist to correct a patient's vision defects due to astigmatism. Additionally, the determination of the curvature of the cornea can be measured during eye surgery by an ophthalmic surgeon to establish the effects of the eye surgery upon corneal curvature at the actual time of surgery. Heretofore, such measurements have been taken using surgical instruments known as ophthalmometers or Keratometers.

Typically, a Keratometer uses a fixed illuminated object placed at a given distance from the anterior surface of the cornea. The distance is held constant by using the focus of a surgical microscope at high power utilizing minimum depth of field. This distance is the focal length of the objective lens of the microscope. The fixed illuminated object will form an image behind the anterior surface of the cornea which will vary depending on the curvature of the cornea. The surgical Keratometer has the ability to measure the size of this very small image accurately. Keratometers may provide quantitative as well as qualitative measurements of the curvature of the cornea in all meridians. A qualitative Keratometer provides the surgeon with an idea of the amount of astigmatism and the shape or gross shape of the cornea. A quantitative surgical Keratometer provides the surgeon with an actual measurement of the radius of curvature of the cornea or the dioptic power of the cornea.

Previously developed instruments for the measurement of the radius of curvature of the cornea include the instruments described in U.S. Pat. No. 4,046,463 issued to La Russa et al on Sept. 6, 1977 and entitled "Indicating an Asphericity of the Cornea of an Eye"; U.S. Pat. No. 4,157,859 issued to Terry on June 12, 1979 and entitled "Surgical Microscope System"; and U.S. Pat. No. 4,165,744 issued to Cravy et al on Aug. 28, 1979 and entitled "Dynamic Keratometry and Keratoscopy Method and Apparatus".

The La Russa et al instrument also known as the Troutman Keratometer, provides a qualitative measurement of the radius of curvature of the cornea. The Troutman Keratometer projects a circle of discontinuous dots upon the surface of the cornea. The degree of distortion of the dot pattern relative to a perfect circle is established by comparing the relationship between the dot pattern and a microscope eyepiece reticles. A flat cornea reflects a dot pattern closer to the outer reticle of the eyepiece, while a steep cornea reflects a dot pattern closer to the inner reticle. The maintenance of the Troutman Keratometer at a fixed distance from the cornea thus provides a measure of the degree of corneal curvature. Adjusting the cross hairs of the reticle of the microscope to coincide with the long axis of a reflected oval dot pattern provides reference points for establishing the approximate amount of astigmatism or meridional error present. Since image focus and measurement of the degree of corneal curvature require that the Troutman Keratometer be fixed, the system is incapable of providing dynamic keratometry. That is, it is not possible to dynamically detect meridional error of all positions of the meridian lying between the cornea center and corneal periphery. The focused dot pattern crosses each corneal meridian at only one point.

The Terry surgical microscope system projects onto the surface of a cornea a circular image and utilizes a prism for optically splitting the image so projected into a plurality of substantially identical images viewable through one or both binocular eyepieces of a microscope. By using the zoom mechanism of the microscope or by utilizing rotary prisms, the system positions the images in a predetermined alignment for indicating the curvature and configuration of the cornea. The projected image may be optically split by using prisms, lenses or mirrors insertable into the optical path within the microscope. Where a fixed location prism array is utilized for optically splitting the image, the optical system of Terry is adjusted by varying the magnification powers of the microscope to bring the projected image and split images into a predetermined alignment and configuration. Where rotating prisms are utilized in a fixed position within the optical path for optically splitting the image, the optical system of Terry is adjusted by varying the prism power to bring the images into a predetermined alignment and configuration. The Terry system is a quantitative Keratometer in which the radius of curvature of the cornea is calculated.

The Cravy instrument is also a qualitative device for determining corneal curvature. The Cravy instrument projects a continuous circle of light onto the surface of a cornea from a housing for viewing the reflected image. The housing is moved toward the cornea so that the image is reflected from more peripheral portions of the cornea, such that the diameter of the reflected image progressively increases toward the cornea periphery to detect meridional errors through the angular length of the meridians of the image.

Such previously developed surgical instruments for measuring the radius of curvature of a cornea have been relatively complex in structure, difficult to manufacture and expensive. Additionally, qualitative Keratometers do not provide the ophthalmic surgeon with sufficient information to correct for corneal defects. The use of previously existing quantitative surgical Keratometers such as the Terry Keratometer depends upon the zoom feature of a microscope which must be used with the Keratometer and further requires modification of the microscope. Therefore, such a Keratometer is dependent upon the operation and the components of the associated microscope. An important quality of a Keratometer must be its accuracy. The accuracy of a surgical Keratometer is two fold, one being the absolute accuracy and the other being a relative accuracy. The absolute accuracy of the Keratometer is the value of the reading of a meridian compared to the actual value of the specific meridian and depends on the accuracy of focusing of a microscope. If the microscope is not absolutely focused, then the Keratometer cannot read an absolute value which presents a problem for fitting contact lenses. The important measurement for astigmatism control is the difference in value of the two major meridians, usually vertical and horizontal. The difference of the two values determines the astigmatism and can be controlled by closure techniques for closing the cornea at the end of corneal surgery. This accuracy reflects the relative accuracy which, because the measurements are taken at the same focal length, tends to result in relatively high accuracy. Due to these requirements, such surgical instruments require a high degree of accuracy. Additionally, since such surgical instruments are utilized during surgery, they must be easy to operate and provide immediate information to the ophthalmic surgeon.

A need has thus developed for a surgical instrument for measuring the radius of curvature of a cornea that does not depend on the optics of a microscope thereby eliminating the need for zoom microscopes. A need has further arisen for a surgical instrument that can be mounted on any existing microscope without interfering with the operation of the microscope during surgery or during normal measurement procedures. A need has further arisen for a surgical instrument for measuring the radius of curvature of a cornea which is accurate, both absolutely and relatively, reliable and inexpensive resulting in a maintenance free instrument.

DISCLOSURE OF INVENTION

In accordance with the present invention, a surgical instrument for measuring the radius of curvature of the cornea is provided resulting in a reliable, accurate and relatively inexpensive instrument which is adapted for use with operating microscopes and which eliminates the problems heretofore associated with such measuring instruments.

In accordance with the present invention, a device for measuring the radius of curvature of a cornea includes structure for projecting a reference image on the cornea. The reference image is substantially a circle having a diameter and is composed of discontinuous dots. A rod of refractile transparent material is positioned for optically forming two images substantially identical to the reference image. Structure is provided for varying the diameter of the reference image and the two images substantially identical to the reference image, such that the images form a predetermined image pattern. Structure is further provided for measuring the diameter of the reference image when the predetermined image pattern is formed to provide an indication of the radius of curvature of the cornea.

In accordance with another aspect of the present invention, in an optical instrument employing a microscope adapted to bring into focus the cornea of a patient's eye to provide a reference distance in connection with the measurement of the radius of curvature of the cornea, a surgical instrument includes structure for projecting a reference image on the cornea disposed in a plane perpendicular to the optical axis of the eye and of the microscope. A rod of refractile transparent material is positioned in the field of view of the microscope with a diagonal of the cross-section thereof common to the optical axis of the microscope for optically forming two images substantially identical to the reference image as viewed through the rod. Structure is further provided for varying the size of the images, such that the images form a predetermined image pattern. Measuring structure is provided for measuring the reference image when the predetermined image pattern is found to thereby provide an indication of the radius of curvature of the cornea.

In yet another aspect of the present invention, a Keratometer is provided and includes a housing. Structure is mounted within the housing for projecting a reference circle having a diameter and comprising discontinuous dots of light onto a cornea for reflection of a generally circular image from the cornea along an axis perpendicular to the cornea. A rod of refractile transparent material is disposed within the housing and mounted along the axis for receiving the reflection from the cornea to optically form two image circles substantially identical to the reference circle of discontinuous dots when viewed through the rod. Structure is provided for varying the diameter of the circles, such that the reference circle is disposed tangent to the image circles along a line. Structure is further provided for measuring the diameter of the circles when aligned tangent to one another.

In yet another aspect of the present invention, a method for the measurement of the curvature of the cornea of an eye is provided. The method includes the step of establishing an object pattern comprising a reference circle having a diameter and being composed of discreet dots positioned for reflection from the cornea. The reference circle is projected on the surface of the cornea. A further step includes viewing the reflection of the reference circle from the cornea through a refractile transparent rod at a reference position where a medial diagonal of the rod is located at the line of site of the pattern to thereby optically form two images of the reference circle viewed through the rod. The diameter of the reference circle is then varied, such that the image circles lie tangent to the reference circle. An additional step includes measuring the diameter of the reference circle in the tangent position to provide an indication of the curvature of the cornea.

BRIEF DESCRIPTION OF DRAWINGS

For a more complete understanding of the present invention and for further advantages thereof, reference is now made to the following Detailed Description taken in conjunction with the accompanying Drawings in which:

FIG. 1 is a side elevational view of the present surgical instrument of the present invention;

FIG. 1A is a top plan view of the present surgical instrument illustrated in FIG. 1;

FIG. 2 is a schematic elevational view of a microscope system utilizing the present surgical instrument;

FIG. 3 is an enlarged view of the rod utilized with the present surgical instrument;

FIG. 4 illustrates a view of the image pattern in a vertical meridian generated by the present surgical instrument;

FIG. 5 illustrates a view of the image pattern in a horizontal meridian generated by the present surgical instrument;

FIG. 6 is a top plan view of an image producing plate utilized in the present surgical instrument;

FIG. 7 is a top plan view of an image producing plate utilized in the present surgical instrument;

FIG. 8 is a top plan view of the image producing plates of FIGS. 6 and 7 superimposed in a first position;

FIG. 9 is a top plan view of the image producing plates of FIGS. 6 and 7 superimposed in a second position;

FIG. 10 illustrates an image pattern generated by the present surgical instrument in a vertical meridian for measuring the radius of curvature of a cornea;

FIG. 11 illustrates an image pattern generated by the present surgical instrument in a horizontal meridian for measuring the radius of curvature of a cornea;

DETAILED DESCRIPTION

Figure 12:
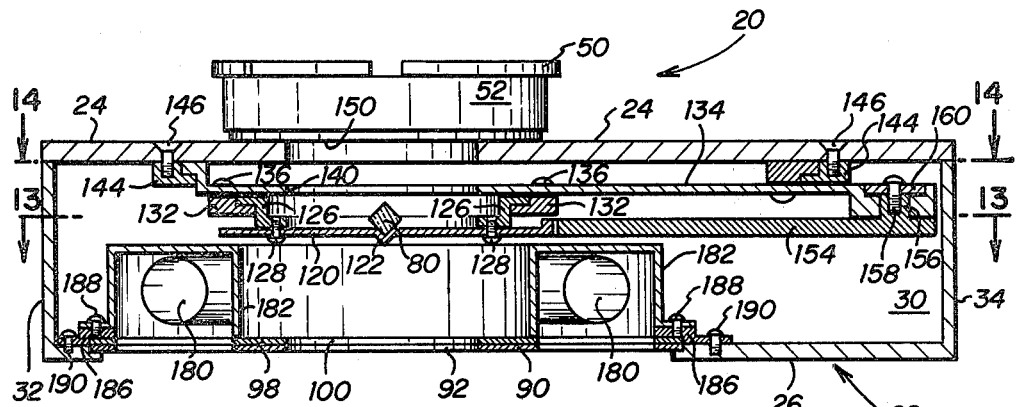
FIG. 12 is an enlarged cross-sectional view taken generally along sectional lines 12—12 of FIG. 1A.

FIG. 1 and FIG. 1A illustrates the present surgical instrument for measuring the radius of curvature of a cornea of an eye and is generally identified by the numeral 20. Instrument 20 includes a housing generally identified by the numeral 22. Housing 22 is generally rectangular in shape and includes a top wall 24, bottom wall 26, side wall 28, side wall 30 and end walls 32 and 34. Extending from end wall 34 is a micrometer 36 which engages structure within housing 22 for measuring the object size which is projected by instrument 20 on the cornea of an eye. Micrometer 36 is calibrated such that the dioptic power of the cornea can be calculated which is displayed on a display 38.

Disposed within side 28 of housing 22 is a slot 40 which receives a handle 42 which is slidable horizontally therein. Handle 42 is utilized for controlling structure 22 to be subsequently described within housing 22 for measuring the radius of curvature of the cornea along a plurality of meridians. A scale 46 is provided above slot 40 for indicating the angle of the meridian at which the radius of curvature of the cornea is measured which is indicated by the placement of handle 42.

Mounted to top wall 24 of housing 22 is a cylindrical adapter 50 which is provided in a configuration suitable to be clamped as by a screw clamp 52 to the housing of a microscope objective lens.

Referring now to FIG. 2, an ophthalmologist's microscope 56 is illustrated in position for viewing the cornea 58 of an eye 60 of a patient. Interconnected to microscope 56 utilizing cylindrical adapter 50 and screw clamp 52 is surgical instrument 20 such that microscope 56 can view cornea 58 through surgical instrument 20. Contained within housing 22 of surgical instrument 20 is a light source which transmits light in the general direction of eye 60 along path 64. Light is reflected from the surface of cornea 58 upwardly through surgical instrument 20 to be viewed by microscope 56 along path 66 and the optical axis of microscope 56 identified by numeral 68. The distance between cornea 58 and the lens of microscope 56 is the focal length (F.L.) which is noted in FIG. 2.

Surgical instrument 20 generates as will subsequently be described with respect to FIGS. 6-9 a reference image 70 for projection on cornea 58 of eye 60. Reference image 70 is substantially a circle composed of discontinuous dots of light. Reference image 70 is projected utilizing the light source disposed within housing 22 of surgical instrument 20.

Mounted within housing 22 of surgical instrument 20 is a rod 80 (FIG. 1A). Rod 80 is illustrated in cross-section in FIG. 3 and more fully illustrated in FIG. 13. Rod 80 is composed of a transparent refractile material and is illustrated in FIGS. 3 and 13 as being square for illustrative purposes; however, a prism and for example, a double edge prism can also be utilized with the present invention. As used throughout the present Description, the term rod shall include a prism structure. As will subsequently be described with respect to FIGS. 12 and 13, rod 80 is disposed within housing 22 along the optical axis 68 of microscope 56, such that the reflection of reference image 70 passes through rod 80 for viewing by the objective lens of microscope 56. When viewing reference image 70 through rod 80 using microscope 56, a double image of reference image 70 will be viewed.

FIGS. 4 and 5 illustrate two positions of the image pattern viewed through rod 80 of reference image 70 by microscope 56. FIG. 4 illustrates the image pattern created with rod 80 in a predetermined position for measuring the vertical meridian of the cornea 58 of eye 60 while FIG. 5 illustrates the image pattern generated when rod 80 is in a position for measuring the horizontal meridian of cornea 58 of eye 60. FIGS. 4 and 5 illustrate reference image 70 as having a substantially circular configuration composed of discontinuous dots of reflected light 82. Twelve dots 82 are shown for illustrative purposes only, the number of dots 82 is a matter of design choice.

Due to operation of rod 80, reference image 70 is optically split to form split images 70a and 70b located adjacent reference image 70, such that the centers of images 70, 70a and 70b fall on a line. Each image 70, 70a and 70b has the same diameter, indicated in FIGS. 4 and 5 by the designation d. The distance between the centers of images 70 and 70a and images 70 and 70b is determined by the length, L of the side of rod 80 (FIG. 3), its index of refraction and its angular relation to the optical axis 68. The distance between centers of images 70, 70a and 70b is therefore a known quantity in the measurement process of determining the radius of curvature of cornea 58 utilizing surgical instrument 20.

Referring simultaneously to FIGS. 6 and 7, the structure of surgical instrument 20 for projecting and generating reference image 70 will now be discussed, in part. Referring initially to FIG. 6, disposed within housing 22 of surgical instrument 20 is an image production plate generally identified by the numeral 90. Image production plate 90 is illustrated as being generally circular; however, plate 90 may be of any shape so long as the pattern illustrated in FIG. 6 is contained thereon. Image production plate 90 is disposed in bottom wall 26 of housing 22 and is fixedly maintained in bottom wall 26.

The pattern illustrated in FIG. 6 may also be fabricated directly on bottom wall 26. Image production plate 90 is substantially opaque except for a central area or aperture 92 and linear radially extending segments 94. Aperture 92 and segments 94 are non-opaque whereas the portion of plate 90 disposed between segments 94 is opaque. The radial orientation of segments 94 corresponds to the displacement between dots 82 (FIG. 4) comprising reference image 70. Segments 94 are circumferentially disposed around aperture 92 and are approximately two centimeters in length and two millimeters in width. Plate 90 is disposed within housing 22 such that the center of aperture 92 aligns with optical axis 68 of microscope 56 (FIG. 2).

FIG. 7 illustrates an image production plate generally identified by the numeral 98 which is disposed within housing 22 above image production plate 90 (FIG. 6). Image production plate 98 is substantially circular as illustrated in FIG. 7 and substantially opaque. Disposed centrally within image production plate 98 is a central area or aperture 100 of non-opaque material, such that the center of aperture 100 aligns with optical axis 68 of microscope 56. Radially disposed around aperture 100 are curvilinear radial non-opaque segments 102 whose ends lying closest to aperture 100 are in the same general position as the corresponding ends of segments 94 of image production plate 90. All areas between segments 102 are opaque except for aperture 100. Segments 102 are circumferentially disposed around aperture 100 and are approximately 2.5 centimeters in length and two millimeters in width.

Image production plate 98 is disposed for rotation within housing 22 of surgical instrument 20 as will subsequently be described by using micrometer 36. To effectuate such rotation, an arm (not shown) is attached to micrometer 36 and to image production plate 98 along the circumference thereof at location 104.

The curvature of segments 102 is selected such that there is a linear relationship between the rotation of image production plate 98 and the rotation of micrometer 36.

Image production plates 90 and 98 may be fabricated on a thin piece of photographic film or, for example, a glass or plastic sheet of material. The medium for image production plates 90 and 98 only requires that light can pass unobstructed through aperture 92 and aperture 100 and segments 94 and 102 of image production plates 90 and 98, respectively.

Referring now to FIGS. 8 and 9, the operation of image production, plates 90 and 98 will be described. As previously stated, image production plate 90 is disposed in bottom wall 26 of housing 22. Image production plate 98 is disposed immediately above image production plate 90 and aligned such that aperture 100 lies on top of aperture 92 of image production plate 90. It therefore can be seen from FIG. 8 that portions of segments 94 of image production plate 90 will be covered by the opaque portions lying between segments 102 of image production plate 98. However, a certain portion of segments 94 of image production plate 90 will overlap with segments 102 of image production plate 98 such that light passing through image production plates 90 and 98 will be unoccluded. These portions of segments 94 and 102 through which light can pass correspond to dots 82 (FIG. 4) comprising the circular reference image 70 generated by surgical instrument 20. Light is occluded from passing through portions of segments 102, such as 102a and 102b due to the opaque areas between segments 94 of image production plate 90 overlapping portions 102a and 102b of segment 102 of image production plate 98.

It can be seen by referring to FIG. 9, that the position of the unoccluded portions of segments 94 and 102 corresponding to dots 82 (FIG. 4) can be changed by rotation of image production plate 98. As illustrated in FIG. 9, image production plate 98 has been rotated in the direction of arrow 106 such that the unoccluded portions of segments 94 and 102 corresponding to dots 82 has now moved outwardly from the center of aperture 100 such that the resulting diameter of reference image 70 formed by dots 82 is greater in FIG. 9 than in FIG. 8. Therefore, it can be seen that the interaction between non-opaque segments 94 of image production plate 90 and non-opaque image segments 102 of image production plate 98 will produce the 12 discontinuous dots 82 of reference image 70 and will produce various diameter circles of reference image 70. The ability to vary the diameter or size of reference image 70 is an important aspect of the present invention as this diameter is a measurable quantity utilized in determining a radius of curvature of the cornea and which is adjustable utilizing the present surgical instrument 20 to create a predetermined pattern between reference image 70 and the optically split images 70a and 70b.

Referring simultaneously to FIGS. 4 and 10, the effect of rotation of image production plate 98 is illustrated. The centers of the circle of dots 82 comprising reference image 70, split image 70a and split image 70b are in the same locations in FIG. 4 as in FIG. 10. However, the diameters, d' of the circles in FIG. 10 have increased due to rotation of image production plate 98 as illustrated in FIG. 9, such that the circle of dots 82 comprising reference image 70 lies tangent with the circles of discontinuous dots 82 comprising split image 70a and split image 70b. The change in diameter, d' minus d (FIG. 4) can be measured by the rotation of image production plate 98 by micrometer 36 to provide an indication of the radius of curvature of the cornea or dioptic power of the cornea.

Referring simultaneously to FIGS. 5 and 11, it can be seen that measurement of the radius of curvature of the cornea in the horizontal meridian can also be effected by enlarging the diameter of reference image 70, split image 70a and split image 70b such that the circles of discontinuous dots 82 touch.

The radius of cornea 58 is determined in accordance with the geometrical relationships expressed in the following equation:

$$r = 2(F.L.)I/O; \qquad (1)$$

where:
  r = the radius of curvature of the cornea;
  F.L. = the focal length in the microscope objective lens (FIG. 2);
  O = size of object projected on cornea; and
  I = size of image produced by cornea determined by size of rod 30. An addition geometrical relationship for the radius of curvature of a cornea is given by:

$$r = 337.5/K; \qquad (2)$$

where:
  r = the radius of curvature of the cornea;
  337.5 = difference of index of refraction for the cornea and air; and
  K = dioptic power of the cornea.

The substitution for the value of r in Equation 1 for the value of r in Equation 2 yields that:

$$K = C(O); \quad (3)$$

where:
K=dioptic power of the cornea;
C=constant known quantity being $337.5/2(F.L.)I$; and
O=size of object.

Therefore, since the focal length (FIG. 2) is known and the size of the image is known, the radius of curvature of the cornea and dioptic power can be calculated by measuring the object size which is accomplished by the present surgical instrument 20 by the rotation of image production plate 98.

In summary, the dimension of cornea 58 to be measured is a product of the prismatic deviation caused by rod 80 and the distance between microscope 56 and cornea 58, the focal length both of which are known quantities. The size and shape of reference image 70 which is reflected off cornea 58 is proportional to the radius of corneal curvature. The use of rod 80 produces a dual image of reference image 70, split image 70a and 70b. When reference image 70 and split image 70a and split image 70b "touch" the corneal curvature is determined by the size of the reference image 70 projected on cornea 58 of eye 60 (FIG. 1). With a known focal length, and a known prismatic deviation between reference image 70 and split image 70a or split image 70b, the size of the corneal curvature is proportional to the diameter of the reference image 70 when reference image 70 is tangential to or touching split image 70a and split image 70b.

Figure 13:
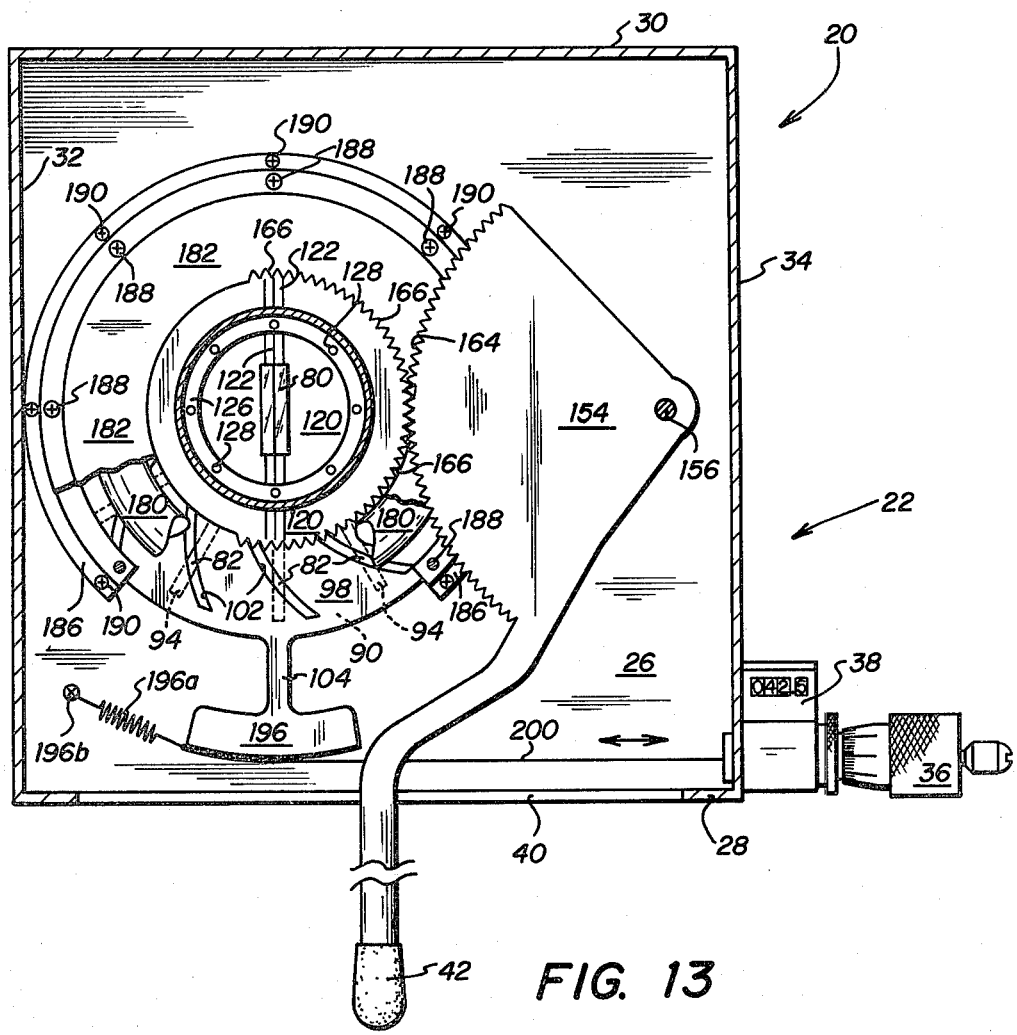
FIG. 13 is a sectional view taken generally along sectional lines 13—13 of the surgical instrument illustrated in FIG. 12.

Referring simultaneously to FIGS. 12 and 13, wherein like numerals are utilized for like and corresponding components, the structure of surgical instrument 20 for creating reference image 70 and for generating the image pattern wherein reference image 70 touches split image 70a and split image 70b (FIGS. 10 and 11) will now be described. Rod 80 is mounted on a disk 120. Disk 120 includes a triangular recess 122 for supporting rod 80 with its cross-sectional diagonal coinciding with the optical axis 68 of microscope 56 (FIG. 1). Disk 120 may be opaque or translucent or may be a ring structure to support rod 80. Rod 80 may have a length L (FIG. 3) of about, approximately 3 millimeters to about 7 millimeters depending on a size of the cornea to be measured.

Disc 120 is mounted to a bracket 126 using screws 128. Bracket 126 engages a bracket 132 for mounting disk 120 to a sliding plate 134 using screws 136. Sliding plate 134 includes a U-shaped cut-out 140, such that vision through rod 80 is unobstructed by the presence of sliding plate 134. Sliding plate 134 is received in a track 144 which is mounted to top wall 24 of housing 22 using screws 146.

Disposed within top wall 24 of housing 22 is an aperture 150. It therefore can be seen that there is a clear line of sight through surgical instrument 20 for viewing cornea 58 through an objective lens contained within microscope 56 since there is a clear viewing passage through cylindrical adapter 50, screw clamp 52, aperture 150, cut-out 140, rod 80, disk 120, aperture 100 and aperture 92 all of which are centered around optical axis 68 of microscope 56.

Still referring simultaneously to FIGS. 12 and 13, handle 42 extends into an arm 154. Arm 154 includes a boss 156 which receives a screw 158 and retainer 160 for rotatably mounting arm 154 to sliding plate 134.

One side of arm 154 includes a plurality of teeth 164 for mating with teeth 166 circumferentially disposed around disk 120. It therefore can be seen that the horizontal sliding of handle 42 within slot 40 (FIG. 1) causes rotation of disk 120 such that rod 80 rotates for measuring the radius of curvature of cornea 58 along a plurality of meridians passing through the center of cornea 58 which also pass through the optical axis 68 of microscope 56. The meridian along which a radius of curvature of cornea 58 is measured is indicated by the position of handle 42 with respect to scale 46 (FIG. 1).

Mounted within housing 22 of surgical instrument 20 is a light source 180. Light source 180 may comprise, for example, a spherical fluorescent tube which is disposed above segments 102 of image production plate 98 to thereby shine through the unoccluded portions of segments 94 and segments 102 of image production plate 90 and image production plate 98, respectively. Light source 180 is contained within a shroud 182. Shroud 182 is mounted to the top of a track 186 using screws 188. Track 186 is mounted to bottom wall 26 of housing 22 using screws 190.

Image production plate 98 is mounted within track 186 for rotational movement therein. Rotation of image production plate 98 in track 186 is accomplished using an arm 196 which is interconnected to location 104 of image production plate 98. Rotation of image production plate 98 is effected by rotation of micrometer 36 which in turn moves a wire 200 to impart rotational motion to arm 196. Return movement of arm 196 is imparted by spring 196a whose one end is mounted to arm 196 and the other end to bottom plate 26 by a screw 196b. As previously described, rotation of image production plate 98 causes the diameter of the circle forming reference image 70 to increase or decrease until reference image 70 touches split reference image 70a and 70b. The distance required to produce this tangency is a function of the radius of curvature of cornea 58 and can be read on display 38. Display 38 may be calibrated to read directly in diopters such as, 042.5 diopters as illustrated in FIG. 13.

Figure 14:
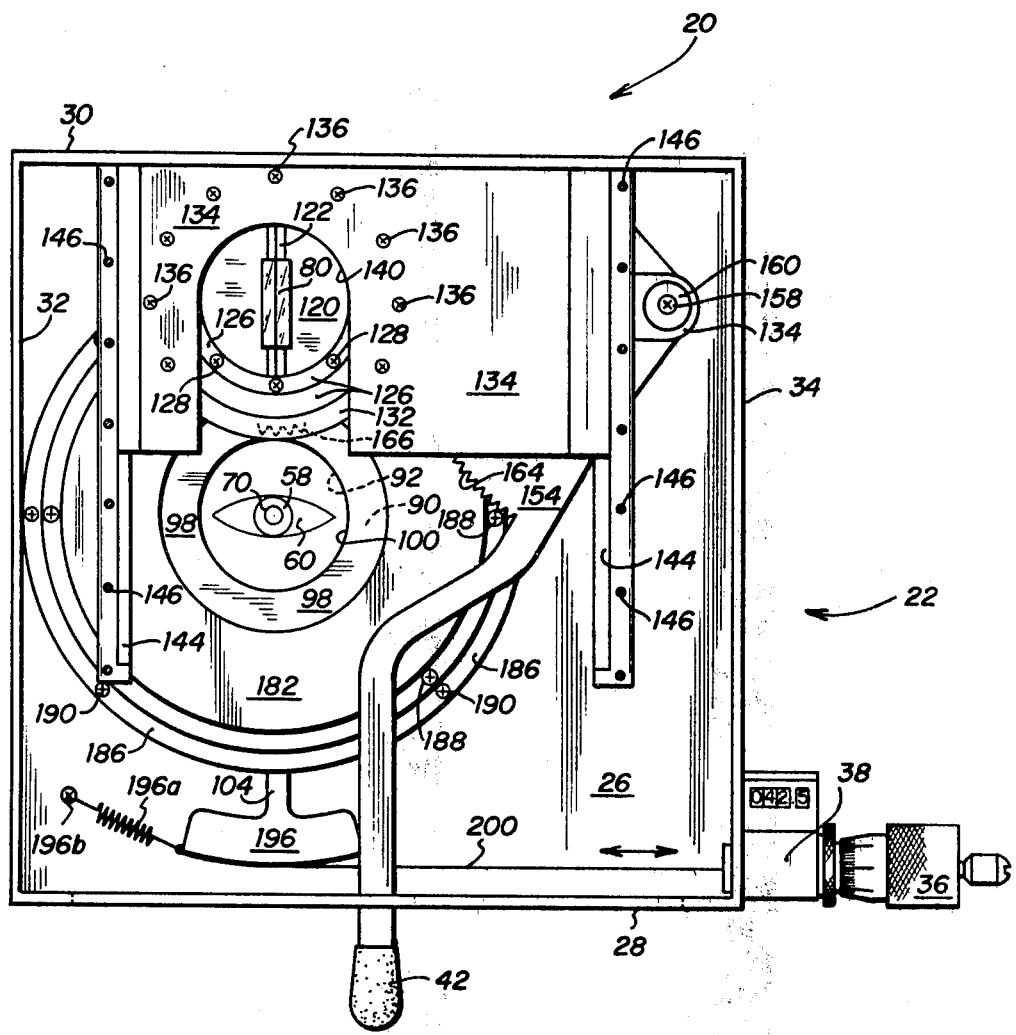
FIG. 14 is a cross-sectional view taken generally along sectional lines 14—14 of the surgical instrument illustrated in FIG. 12 with the refractile rod displaced.

Referring simultaneously to FIGS. 13 and 14, wherein like numerals are utilized for like and corresponding components previously identified, handle 42 is also utilized for moving rod 80 out of the field of view of microscope 56. In this manner, reference image 70 can be viewed as reflected by cornea 58 without split images 70a and 70b. By pushing handle 42 rearwardly, sliding plate 134 is slid within track 144 such that sliding plate 134 contacts side wall 30 of housing 22. Since rod 80 is mounted within disk 120 and disk 120 is mounted through brackets 126 and 132 to sliding plate 134, motion of sliding plate 134 will remove disk 120 from the field of view of microscope 56.

Although surgical instrument 20 has been illustrated for use with a monocular microscope 56, surgical instrument 20 can be equally utilized with a binocular microscope. In such usage, rod 80 and image production plates 90 and 98 will be positioned relative to the optical axis of one of the objective lenses of the binocular microscope such that the other lens of the binocular microscope will be unobstructed by rod 80 and the unobstructed objected lens can therefor view reference image 70 without being split. It should also be understood that the magnification function of microscope 56 is only utilized for ease in viewing reference image 70 and split reference images 70a and 70b (FIG. 4) and not for a measurement purpose in calculating or determining the radius of curvature of cornea 58.

It therefore can be seen that the present surgical instrument provides for a reliable, accurate and relatively inexpensive instrument which is capable of measuring the radius of curvature of a cornea with a high degree of accuracy. The present surgical instrument is simple to operate and maintain and is adaptive to existing surgical microscopes with a minimum of installation time.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An instrument for measuring the radius of curvature of a cornea of an eye comprising:
   a housing;
   means mounted within said housing for projecting a reference image on the cornea along an axis perpendicular to said cornea, said reference image comprising substantially a circle having a diameter;
   a rod of refractile transparent material disposed within said housing and mounted along said axis for optically forming two images substantially identical to said reference image;
   means for varying the diameter of said reference image and said two images substantially identical to said reference image, such that said images form a predetermined image pattern; and
   means for measuring the diameter of said reference image when said predetermined image pattern is formed to provide an indication of the radius of curvature of the cornea.

2. The instrument of claim 1 wherein said circle is composed of a plurality of discontinuous dots of light.

3. The instrument of claim 1 wherein said means for projecting a reference image on the cornea includes:
   a first plate being generally opaque and having a plurality of linear radial non-opaque segments disposed thereon;
   a second plate being generally opaque and having a plurality of curvilinear radial non-opaque segments disposed thereon; and
   said first and second plates being disposed adjacent one another, such that portions of said plurality of linear radial non-opaque segments and portions of said plurality of curvilinear radial non-opaque segments overlap, said overlapping portions thereby forming substantially a circle of discontinuous non-opaque segments.

4. The instrument of claim 3 wherein said means for varying the diameter of said reference image includes:
   means for rotating said second plate with respect to said first plate, such that said overlapping portions of non-opaque segments of said first and second plates are radially displaced as said second plate is rotated.

5. The instrument of claim 1 and further including:
   means for rotating said rod of refractile transparent material to thereby rotate said images to measure the radius of curvature along a plurality of meridians of the cornea.

6. In an optical instrument employing a microscope adapted to bring into focus the cornea of a patient's eye to provide a reference distance in connection with the measurement of the radius of curvature of the cornea, the combination which comprises:
   means for projecting a reference image on the cornea of the eye disposed in a plane perpendicular to the optical axis of the eye and of the microscope;
   a rod of refractile transparent material mounted in the field of view of the microscope with a diagonal of the cross-section thereof common to the optical axis of the microscope for optically forming two images substantially identical to said reference image as viewed through said rod;
   means for varying the size of said images, such that said images form a predetermined image pattern; and
   means for measuring the diameter of said reference image when said predetermined image pattern is formed to provide an indication of the radius of curvature of the cornea of the eye.

7. The combination of claim 6 wherein said means for projecting a reference image comprises means for generating a substantially circular image having a diameter and being composed of discontinuous dots.

8. The combination of claim 7 wherein said means for varying the size of said images includes means for varying the diameter of said substantially circular image.

9. The combination of claim 8 wherein said means for generating said substantially circular image includes:
   a light source;
   a first plate being generally opaque and having a plurality of linear radial non-opaque segments disposed thereon;
   a second plate disposed adjacent said light source and being generally opaque and having a plurality of curvilinear radial non-opaque segments disposed thereon;
   said first and second plates being disposed adjacent one another, such that portions of the opaque area occlude the passage of light from said light source to the cornea, the unoccluded portions projecting said discontinuous dots onto the cornea.

10. The combination of claim 9 wherein said means for varying the diameter of said substantially circular image includes:
    means for rotating said second plate with respect to said first plate, such that said unoccluded portions of said non-opaque segments of said first and said second plates are radially displaced relative to each other as said second plate is rotated.

11. The combination of claim 9 wherein said light source comprises:
    a circular ring lying in a plane perpendicular to the optical axis of the eye and of the microscope.

12. The combination of claim 6 and further including:
    means for moving said rod of refractile material into and out of the field of view of the microscope.

13. The combination of claim 6 wherein said rod is square in cross-sectional shape.

14. A Keratometer comprising:
    a housing;
    means mounted within said housing for projecting a reference circle having a diameter and comprising discontinuous dots of light onto a cornea for reflection of a generally circular image from the cornea along an axis perpendicular to said cornea;
    a rod of refractile transparent material disposed within said housing and mounted along said axis for receiving said reflection from said cornea to optically form two image circles substantially identical to said reference circle of discontinuous dots when viewed through said rod;

means for varying the diameter of said circles, such that said reference circle is disposed tangent to said image circles along a line; and means for measuring the diameter of said circles when aligned tangent to one another.

15. The Keratometer of claim 14 wherein said means mounted within said housing for projecting a reference circle includes:

a light source;

a first plate being generally opaque and having a plurality of linear radial non-opaque segments disposed thereon;

a second plate disposed adjacent said light source and being generally opaque and having a plurality of curvilinear radial non-opaque segments disposed thereon; and said first and second plates being disposed adjacent one another, such that portions of the opaque area occlude the passage of light from said light source to the cornea, the unoccluded portions projecting said discontinuous dots onto the cornea.

16. The Keratometer of claim 15 wherein said means for varying the diameter of said circles includes:

means for rotating said second plate with respect to said first plate, such that said unoccluded portions of said non-opaque segments of said first and second plates are radially displaced as said second plate is rotated.

17. A method for the measurement of the curvature of the cornea of an eye comprising the steps of:

establishing an object pattern comprising a reference circle having a diameter and being composed of discontinuous dots positioned for reflection from the cornea;

projecting the reference circle onto the surface of the cornea;

viewing the reflection of the reference circle through a refractile transparent rod at a reference position where a medial diagonal of the rod is located at the line of sight of the pattern to thereby optically form two images of the reference circle viewed through the rod;

varying the diameter of the reference circle and the diameter of the image circles, such that the image circles lie tangent to the reference circle; and measuring the diameter of the reference circle in the tangent position.

18. The method of claim 17 wherein the step of establishing an object pattern includes:

projecting a light source through a first opaque plate having a plurality of linear radial non-opaque segments and a second substantially opaque plate having a plurality of curvilinear radial non-opaque segments.

19. The method of claim 18 wherein the step of varying the diameter of the reference circle includes rotating the second plate.

20. The method of claim 17 and further including the step of rotating the rod for measuring the curvature of the cornea at varying meridians of the eye.

* * * * *